United States Patent [19]

Grob et al.

[11] 4,054,414

[45] Oct. 18, 1977

[54] GAS CHROMATOGRAPHIC METHOD FOR THE MULTI-ELEMENTAL MICROANALYSIS OF ORGANIC MATERIALS

[75] Inventors: Robert Lee Grob, Malvern, Pa.; Peter Wilson Rulon, Oxford, N.Y.

[73] Assignee: Villanova University, Villanova, Pa.

[21] Appl. No.: 745,995

[22] Filed: Nov. 30, 1976

[51] Int. Cl.$^2$ .............................................. G01N 31/12
[52] U.S. Cl. .......................... 23/230 PC; 23/253 PC; 23/232 C
[58] Field of Search .......... 23/230 PC, 253 PC, 232 C

[56] References Cited

U.S. PATENT DOCUMENTS

| | | | |
|---|---|---|---|
| 3,304,159 | 2/1967 | Hinsvark | 23/230 PC |
| 3,650,696 | 3/1972 | Eads | 23/230 PC |
| 3,698,869 | 10/1972 | Condon | 23/230 PC X |
| 3,838,969 | 10/1974 | Dugan | 23/230 PC |

Primary Examiner—Robert M. Reese
Attorney, Agent, or Firm—James Albert Drobile

[57] ABSTRACT

Microanalytical method for the simultaneous determination of the elements, carbon, hydrogen, sulfur, chlorine, bromine, iodine and nitrogen in a single, small sample of an organic material, said method comprising the steps of: (a) substantially instantaneously igniting and rapidly and completely combusting a small sample of limited size in a heated combustion zone in a pressurized atmosphere of substantially pure oxygen; (b) conducting the gaseous mixture of combustion products in excess oxygen through a heated equilibrium zone; (c) conducting the effluent from the equilibrium zone through a gas chromatographic separation zone containing an adsorbent material adapted to separate combustion products of the said elements each from the others; (d) conducting the effluent from the separation zone through detecting means to quantitatively and separately measure the amount of the combustion product of each of the elements; (e) calculating from the amounts of the several combustion products the percentage content of each of the elements, carbon, hydrogen, sulfur, chlorine, bromine and iodine, in the organic material; and, for the determination of nitrogen, the additional steps of: (f) conducting at least that portion of the effluent from the said detecting means which contains substantially all of the combustion products of nitrogen, through a heated reduction zone; (g) conducting the effluent from the reduction zone through a cooled nitrogen-adsorption zone; (h) conducting a stream of inert gas through the nitrogen-adsorption zone while raising the temperature of that zone to desorb the nitrogen; (i) conducting the effluent from the nitrogen-adsorption zone, consisting essentially of nitrogen and inert carrier gas, through secondary detecting means to quantitatively measure the amount of nitrogen in the sample, and (j) calculating from the amount measured the nitrogen content of the organic material.

15 Claims, 4 Drawing Figures

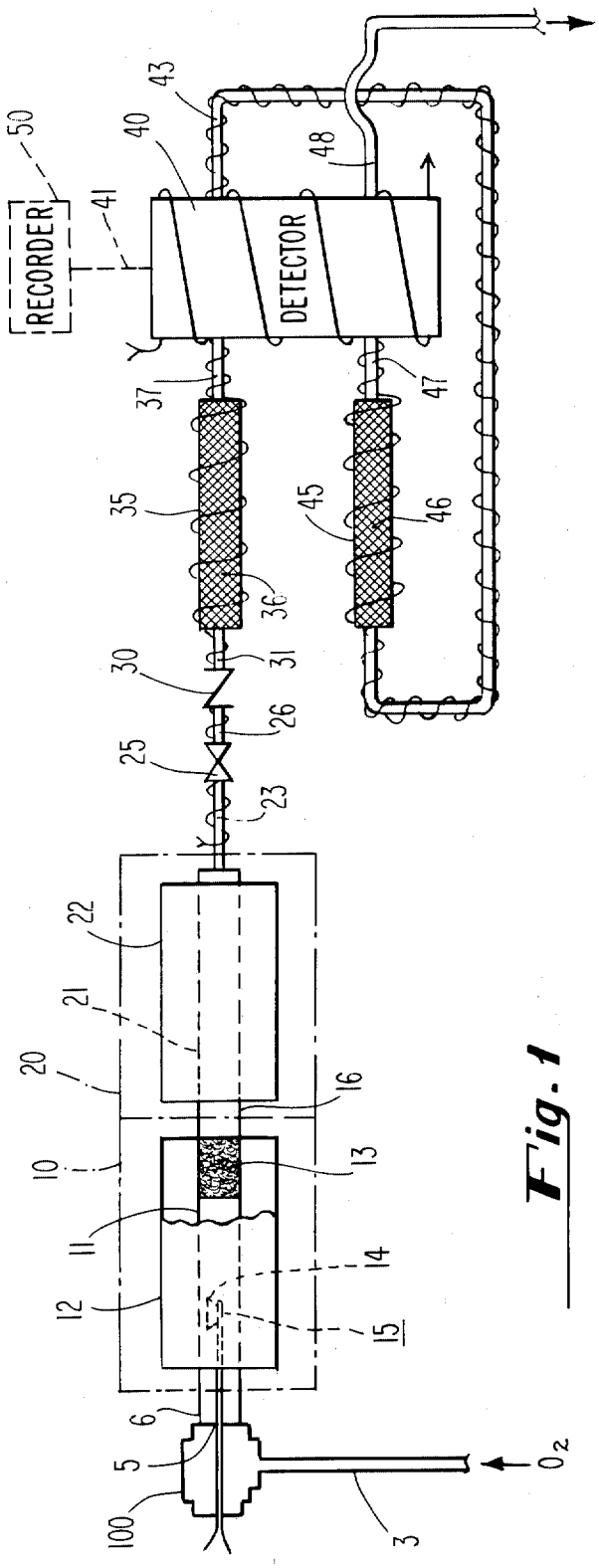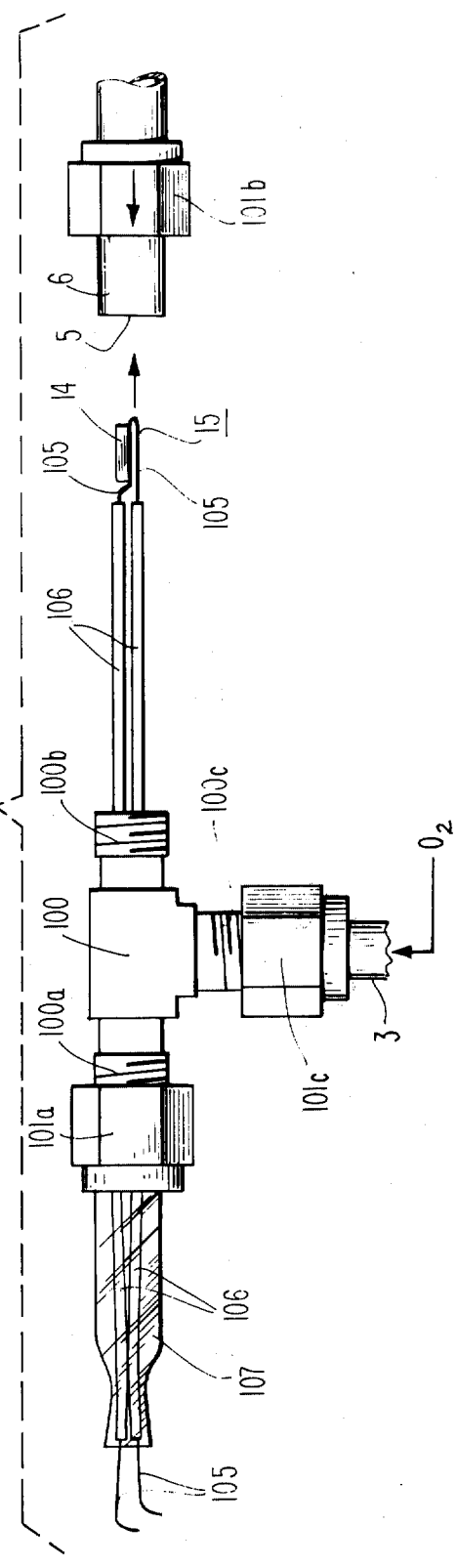

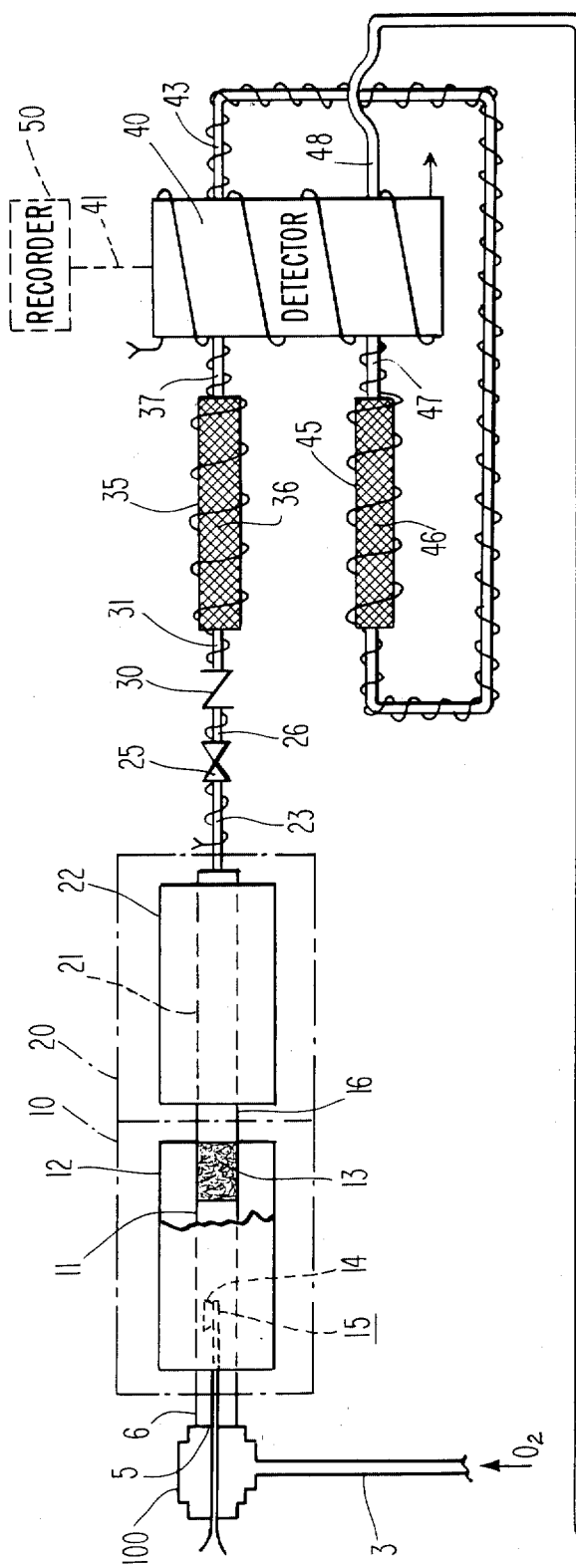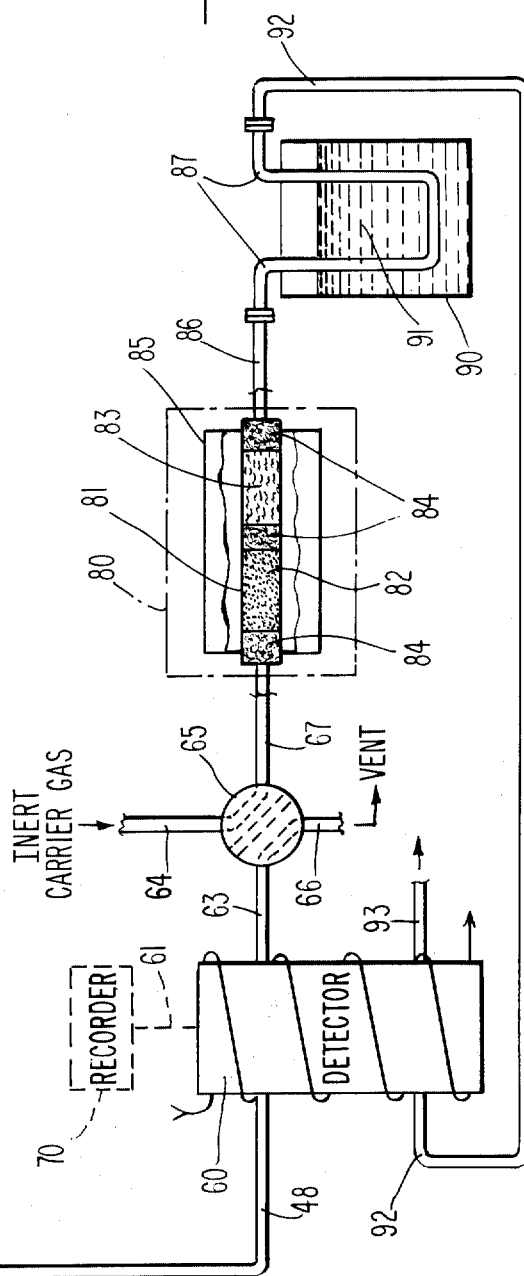
Fig. 2

GAS CHROMATOGRAPHIC METHOD FOR THE MULTI-ELEMENTAL MICROANALYSIS OF ORGANIC MATERIALS

BACKGROUND OF THE INVENTION

1. Field of the Invention

In general, this invention relates to the elemental analysis of an organic material, such as an organic compound or a group of organic compounds. More specifically, the invention relates to methods for the microdetermination of the elements contained in organic materials, by chromatographic study of the products of combustion of such materials. In particular, the present invention is directed to an improved microanalytical method involving a combined combustion and gas chromatographic technique for the simultaneous determination of the elements, carbon, hydrogen, sulfur, chlorine, bromine, iodine and nitrogen in a single, small sample of an organic material.

2. Description of the Prior Art

Elemental analysis of an organic material is a common type of analytical determination which is performed to identify and obtain other information about the material. The elements typically of interest are carbon, hydrogen, sulfur, nitrogen, chlorine, bromine, iodine and oxygen. In some instances, the element phosphorus may also be of interest. Standard micro-methods not involving gas chromatography are available for use in conducting these elemental analyses, but such methods are very time consuming and complicated.

Since gas chromatography is well suited to the separation and quantification of gaseous compounds in mixtures of gases, efforts heretofore have been made to apply a gas chromatographic analytical technique to the separation and quantification of the gaseous products produced by the combustion or pyrolysis of a small sample of the material to be analyzed. However, for a number of reasons these efforts have not been completely satisfactory. For one thing, they have not provided a system which can perform, on a single, small sample, a complete elemental analysis of all of the elements which commonly are present in a majority or organic compounds. Thus, in U.S. Pat. No. 3,304,159, Hinsvark discloses a gas chromatographic analytical method applicable to the combustion products which are obtained from samples including the elements, carbon, hydrogen and nitrogen. Similarly, a combustion-chromatographic method for the quantitative determination of the elements, carbon, hydrogen, nitrogen and sulfur in organic materials is disclosed by Dugan in U.S. Pat. No. 3,838,969. However, heretofore there has been no method which would permit of the microanalytical determination, utilizing a combustion-chromatographic technique, of the elements, carbon, hydrogen, sulfur, chlorine, bromine, iodine and nitrogen from a single, small sample.

SUMMARY OF THE INVENTION

The method of the present invention utilizes a single sample, for example, weighing from 0.5 to 1.2 milligrams, of the organic material to be analyzed. In its simplest form, the method of the present invention permits of the simultaneous determination of the elements, carbon, hydrogen, sulfur, chlorine, bromine and iodine, from this single sample. In an expanded form, involving additional steps, the method of the invention also permits of the determination of the element, nitrogen, in the same sample.

When practiced to analyze a sample of an organic material of one or more of the elements, carbon, hydrogen, sulfur, chlorine, bromine and iodine, the method of the invention comprises: (a) substantially instantaneously igniting and rapidly and completely combusting an accurately-weighted sample of appropriate size in a first heated (combustion) zone in the presence of a contact catalyst and substantially pure oxygen in greater than stoichiometric quantities, (b) conducting the gaseous mixture of combustion products in oxygen through a second heated (equilibrium) zone maintained at a lower but critical temperature, (c) conducting the effluent from the second heated zone through a gas chromatographic separation zone containing an adsorbent which is adapted to separate the combustion products of the said elements each from the others, and (d) conducting the effluent from the gas chromatographic separation zone through suitable detecting means (such as a thermal conductivity detector) to quantitatively and separately measure the amount of the combustion product of each of the elements, and (e) calculating from the amounts of the several combustion products the percentage content of each of the said elements in the organic material of interest.

When practiced to determine the content of nitrogen as well as the other specified elements, the method of the present invention comprises, in addition to the foregoing steps (a) through (e), the steps of: (f) conducting at least that portion of the effluent from the first-named detector which contains substantially all of the combustion products of nitrogen through a heated reduction zone containing a reducing agent, (g) conducting the effluent from the reduction zone through a nitrogen-adsorption zone maintained at a temperature approximating that of liquid nitrogen at atmospheric pressure, (h) conducting a stream of inert gas through the nitrogen-adsorption zone while raising the temperature of that zone to about normal temperature, (i) conducting the effluent from the nitrogen-adsorption zone, consisting essentially of nitrogen in inert gas, through second detecting means which quantitatively measures the amount of nitrogen in the sample, and (j) calculating from that amount the nitrogen content of the organic material.

The substantially instantaneous ignition of the sample is effected preferably through such means as the energization of an electric resistance element, such as Nichrome wire, disposed in close proximity to the sample. The rapid and substantially complete combustion of the sample in the first combustion zone is achieved by the use of a contact catalyst, such as vanadium pentoxide, by the level of the elevated temperature maintained in the combustion zone, and by inserting a plug of quartz wool in the combustion zone downstream of the sample to facilitate the combustion of any carbon particles that may have been entrained in the gaseous combustion products during deflagration. Conditions, particularly temperature, in the so-called equilibrium zone are selected and maintained so as to optimize the formation of sulfur dioxide (rather than sulfur trioxide) in the combustion of sulfur-containing materials.

In the reduction zone, the oxygen carrier gas is eliminated, and the oxides of nitrogen resulting from combustion of nitrogen-containing materials are reduced to molecular nitrogen, by means of a reducing agent (such as copper metal) and appropriate conditions (principally temperature). In the nitrogen-adsorption zone, the molecular nitrogen in inert (e.g., helium) gas carrier is adsorbed and collected, and then desorbed for measurement by an appropriate detector.

The gas chromatographic separating means employed in the practice of the method of this invention are well known, and any apparatus and adsorbent material which are suitable for separating the combustion products of those elements being determined can be used. Likewise, apparatus means for detecting the presence of the separated combustion products of the elements under determination are well known. Apparatus means performing thermal conductivity measurements are particularly useful in the practice of the present invention. Such measurements conveniently are recorded and integrated by any suitable and conventional means and methods.

The use of oxygen, rather than an inert gas like helium, as the carrier gas for conducting the gaseous products from the combustion of the sample through the gas chromatographic analytical system is unique and is beneficial in that, at least with respect to the determination of elements other than nitrogen, no trap or reduction step is required.

BRIEF DESCRIPTION OF THE DRAWINGS

FIG. 1 is a schematic flow diagram illustrating the sequential steps in the practice of the method as applied to the microanalysis of an organic material to determine its content of the elements, carbon, hydrogen, sulfur, chlorine, bromine and iodine, but not nitrogen. This figure also shows, schematically, the preferred arrangement of the various elements of the apparatus utilized in the practice of this mode of the invention.

FIG. 2 is a schematic flow diagram illustrating the sequential steps in the practice of the method as applied to the microanalysis of an organic material to determine its content of the elements, carbon, hydrogen, sulfur, chlorine, bromine, iodine and nitrogen. FIG. 2 also shows, schematically, the preferred arrangement of the various elements of the apparatus utilized in the practice of this mode of the invention.

FIG. 3 is a side elevation of a preferred device combining an igniter, means for introducing the sample and the carrier gas into the combustion zone, and means for supporting the sample during its combustion.

Figure 4:
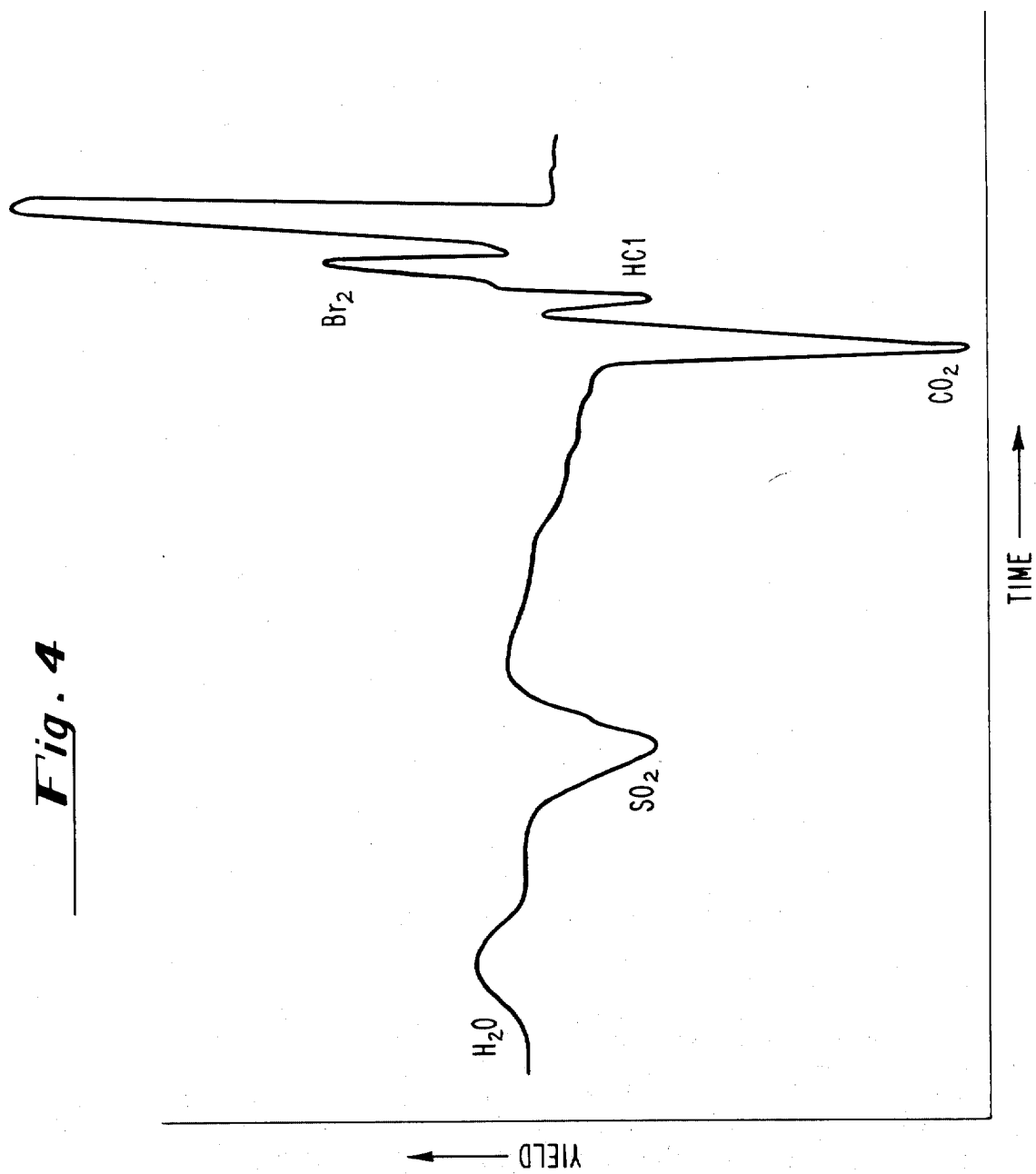
FIG. 4 is a chromatogram illustrating the combustion products obtained from the analysis of p-bromobenzene sulfonyl chloride in the specific embodiment of the invention described hereinafter.

DETAILED DESCRIPTION OF THE INVENTION (including description of preferred embodiments)

Referring to FIG. 1, an aluminum sample boat 14, supported on the end of a Nichrome wire electrical resistance igniter 15, and containing an accurately weighed small sample of the organic material to be analyzed in admixture with a contact combustion catalyst, is inserted through port 5 of conduit 6 into combustion tube or chamber 11 which, together with oven or other heating means 12, comprise heated combustion zone 10. Combustion tube or chamber 11 contains a permeable plug 13 of quartz wool downstream of the igniter 15 and sample boat 14, to ensure the combustion, in chamber 11, of any particulate material, such as carbon particles, generated during deflagration of the sample. Combustion tube or chamber 11 connects directly to equilibrium tube or chamber 21 which, together with oven or other heating means 22, comprise heated equilibrium zone 20. The outlet from equilibrium tube or chamber 21 connects to heated conduit 23 and thence to heated pressure control valve 25, heated conduit 26, heated check valve 30 and heated conduit 31 leading to heated primary chromatographic separation zone or column 35. Column 35 contains an adsorbent material for separating some of the combustion products of the organic material being analyzed, e.g., the polar species, i.e., halogen products. The outlet from column 35 is connected to heated detector 40 through heated conduit 37, and thence to heated secondary chromatographic separation zone or column 45 through heated conduit 43. Column 45 likewise contains an adsorbent material, but one different from that contained in the primary column 35, for separating the remainder of the combustion products of the organic material being analyzed, e.g., the non-polar species, i.e., all products except those of the halogens. The outlet from column 45 is connected to the reference cell of detector 40 through heated conduit 47, and thereafter to vent through conduit 48.

After igniter 15 and the sample of the organic material to be analyzed have been placed in position in combustion tube or chamber 11, and after the port 5 has been sealed with fitting 100 (more fully described hereinafter with reference to FIG. 3), substantially pure oxygen is introduced into the system as a carrier gas through conduit 3 and fitting 100. The oxygen carrier gas flows through conduit 6, combustion tube or chamber 11, conduit 16, equilibrium tube or chamber 21, conduit 23, control valve 25, conduit 26, check valve 30, conduit 31, primary column 35, conduit 37, the sensing cell of detector 40, conduit 43, secondary column 45, conduit 47, the reference cell of detector 40 and conduit 48. The back pressure of the oxygen carrier gas in the combustion chamber 11 and the equilibrium chamber 21 is controlled, through control valve 25, at a pressure in the range of from about 6 p.s.i.g. to about 10 p.s.i.g. Pressures significantly in excess of 10 p.s.i.g. should not be used, however, since they permit combustion to proceed possibly with explosive violence. Furthermore, the flow rate of the oxygen gas through the combustion chamber also is an important factor, and should be within the range of from about 15 to about 35 cm³/min., measured at room temperature or approximately 27° C. Care must be exercised when analyzing for halogens to maintain an oxygen flow rate sufficiently high to prevent the formation of mixed halides. An oxygen flow rate of 20 cm³/min. (measured at about 27° C.) has been found to give excellent results in almost all cases, and is preferred.

Because of the substantially instantaneous ignition and very rapid combustion of the sample in the practice of the method of the present invention, the size of the sample which can be utilized with safety depends upon the size and configuration of the particular apparatus employed and is strictly limited. Thus, it has been found that, in the apparatus used in the specific embodiments hereinafter described, a sample weighing in the range of from about 0.5 milligrams to about 1.2 milligrams gives excellent results and is preferred. Samples weighing significantly in excess of 1.2 milligrams should not be used in that apparatus, since they can combust with explosive violence. A contact catalyst preferably is used and is mixed with the sample in the sample container. Any suitable catalyst can be employed, although vanadium pentoxide has been found to give excellent results.

After the desired flow rate and back pressure of oxygen carrier gas in combustion chamber 11 has been established, igniter 15 is abruptly energized, for example from a central power source adapted to produce a current flow through the igniter of sufficient magnitude to cause the Nichrome wire to glow red in a short period of time, say, in from 3 to 4 seconds. Within a very short period of time, e.g., a couple of seconds, after the igniter 15 has been caused to glow red, the temperature in combustion tube or chamber 11 is brought rapidly to a temperature in the range of from about 675° C. to about 725° C., and preferably 700° C., by means of the oven or other heating means 12 surrounding chamber 11. The energization of igniter 15 and the raising of the ambient temperature in combustion tube or chamber 11 by oven or other heating means 12 causes the sample to ignite substantially instantaneously, and to combust with a flash within a period of 10 seconds or so thereafter. The igniter is permitted to remain energized for a total of approximately 20 seconds before being disconnected, and the elevated temperature produced by oven or other heating means 12 is permitted to hold for an additional 10 seconds or so.

The above-described procedure results in the substantially instantaneous ignition of the sample and its very rapid and substantially complete combustion, thus facilitating the introduction of the products of that combustion into the chromatographic separating column in highly condensed, or "plug", form. Any so-called carbon fog created during this combustion is trapped by a plug of quartz wool 13, positioned downstream of igniter 15 in combustion tube or chamber 11, and there combusted so as to give a quantitative yield of carbon dioxide.

The products of combustion are then transported by the oxygen carrier gas through conduit 16 and into and through equilibrium tube or chamber 21 surrounded by oven or heating means 22. The temperature maintained in equilibrium tube or chamber 21 by oven or heating means 22 is critical to the successful practice of the method of the invention, in that it must functionally preclude the formation of sulfur trioxide ($SO_3$), and typically is in the range of from about 580° C. to about 675° C. Temperatures significantly in excess of 675° C. permit of the conversion of some sulfur dioxide ($SO_2$) to sulfur trioxide ($SO_3$), which is to be avoided, and temperatures significantly below about 580° C. sometimes interfere with the detection of sulfur dioxide ($SO_2$). The over-all conditions obtaining in equilibrium zone 20, including the residence time of the products of combustion in that zone, are adapted to prevent the conversion of any sulfur dioxide ($SO_2$) that might have been present into sulfur trioxide ($SO_3$).

After exiting from equilibrium tube or chamber 21, the products of combustion are transported by oxygen carrier gas through conduit 32, control valve 25, conduit 26, check valve 30, conduit 31 and into primary separating column 35, packed with a suitable adsorbent material 36, where products of combustion are separated each from the others. After removal of the entrained combustion products in column 35, the oxygen carrier gas flows through conduit 43 and into secondary separating column 45, also packed with a suitable adsorbent material 46, and thence from column 45 through conduit 47 and into and through the reference element or cell of detector 40 to provide a reference or base line characteristic of the oxygen carrier gas. Continued flow of the oxygen carrier gas through column 35 causes the separated combustion products to elute from adsorbent material 36 in primary separating column 35, and to pass through conduit 37 and into and through the sensing element or cell of detector 40, where their respective presences and quantities are reflected, for example, by thermal conductivity measurements. Such measurements conveniently can be recorded, in the form of the typical chromatographic chart, or chromatogram, showing the measured property as the ordinate and time as the abscissa, by recording means 50 connected to detector 40 by means 41. Conventional techniques can be employed to convert the chromatogram record into the concentrations of the several elements. For example, the several peaks appearing on the chart, each corresponding to a particular combustion product, e.g., carbon dioxide, water, sulfur dioxide or the like, conveniently can be cut out and separately weighed on an appropriate balance, and appropriate equations used to calculate the percentage elemental composition of the sample from these weights. Of course, recording means 50 also can include automatic integration means.

The several conduits and apparatus elements such as valves, columns and the like conveniently can be heated by electrical resistance wires wrapped thereabouts, and such heat can be controlled by one or more variable rheostats. A suitable temperature is 125° C.

Referring now to FIG. 2, the flow diagram for the microanalysis of an organic material for elements including nitrogen is shown essentially as the combination of a downstream nitrogen reduction train with the flow diagram of FIG. 1 for the determination of elements not including nitrogen. Thus, in FIG. 2, the nitrogen reduction train comprises a second detector 60 connected through connecting means 61 to recorder 70, a gas sampling valve 65, reduction zone 80 comprising reduction tube or chamber 81 surrounded by oven or other heating means 85, nitrogen-adsorption column 87 immersed in container 90 containing a coolant 91 such as liquid nitrogen or dry ice, and appropriate heated connecting conduits. Reduction tube or chamber 81 is segmentally packed with a reducing agent regenerator and oxygen scavenger 82 such as carbon powder, and a reducing agent 83 such as copper metal turnings, which are shown as being separated and contained by three quartz wool plugs 84.

In operation, the products of combustion transported by the oxygen carrier gas pass from primary detector 40 through heated conduit 48 and into and through the reference cell of secondary detector 60, and through conduit 63 and into heated gas sampling valve 65. Normally, gas sampling valve 65 is set so that the combustion products and oxygen carrier gas pass outward through conduit 66 to a vent. When the gas sampling valve 65 is in this normal position, an inert carrier gas, typically helium, is introduced through conduit 64 to gas sampling valve 65, and flows through conduit 67, reduction tube or chamber 81, conduit 86, nitrogen-adsorption column 87, conduit 92, secondary detector 60, and conduit 93 to vent. This flow of inert carrier gas serves to purge the system.

In practice, the nitrogen-adsorption column 87 is submerged in container 90 filled with a suitable coolant such as dry ice or liquid nitrogen 91 which is adapted to maintain a temperature of −30° C. or below, just prior to ignition of the sample contained in sample boat 14. When the chromatogram peak corresponding to carbon dioxide first appears on primary recorder 50, gas sampling valve 65 is manipulated to change the flow patterns to permit the products of combustion, including the oxides of nitrogen, in oxygen carrier gas to flow from conduit 63, through gas sampling valve 65, through conduit 67 into reduction zone 80 and specifically into reduction tube or chamber 81, where, under the influence of regenerator and scavenger 82, reducing agent 83, and a temperature maintained in the range of from about 500° C. to about 600° C., the oxides of nitrogen are reduced to elemental nitrogen and the oxygen carrier gas is converted to carbon dioxide. The gas sampling valve 65 is held in this position, i.e., permitting the flow of the gaseous combustion products in oxygen through the valve and through the nitrogen reduction train, for a short period of time, e.g., about 30 seconds, following which valve 65 is returned to the so-called normal position. After the base line in secondary recorder 70 has stabilized, say, in about 2 minutes, the coolant bath of liquid nitrogen or the like 91 contained in container 90 is removed from nitrogen-adsorption column 87, thus permitting the column gradually to come to ambient room temperature. As the column 87 approaches room temperature, the elemental nitrogen is desorbed and flows through conduit 92 and into secondary detector 60, where its presence and amount are sensed, as by thermal conductivity measurements. Such measurements then can be recorded in secondary recorder 70. The peak formed on the chromatogram, and which corresponds to nitrogen, conveniently can be cut out and weighed as was done in previous analyses involving other elements.

In the combustion step of the method of the present invention, the carbon in the organic material is converted to carbon dioxide, the hydrogen to water, the sulfur to sulfur dioxide, the iodine to molecular iodine, the chlorine to hydrogen chloride, the bromine to molecular bromine, and the nitrogen to various oxides of nitrogen. As mentioned above, a convenient way for measuring the quantity of each of these combustion products (other than the oxides of nitrogen) is to quantify the area under the corresponding chromatogram peak. These quantities then can be converted back to an elemental content. However, the calculation for hydrogen in an organic material than also contains chlorine requires a correction in order to account for the hydrogen which is used to form hydrogen chloride with the chlorine present. An example involving the analysis of the compound, N-chlorosuccinimide, $C_4H_4ClNO_2$ (M.W. 133.54), will illustrate this correction. This compound has the following theoretical elemental composition: carbon—35.97 weight percent; hydrogen—3.02 weight percent; chlorine—26.55 weight percent; and nitrogen—10.49 weight percent. A multi-elemental microanalysis in accordance with the method of the present invention indicates that the elemental composition of a sample of this compound is as follows: carbon—35.97 weight percent; hydrogen—2.27 weight percent; chlorine—26.55 weight percent; and nitrogen—10.49 weight percent. From this latter data, an empirical formula of $C_4H_3ClNO_2$ would be indicated. However, since we know that for each atom of chlorine we have consumed 1 atom of hydrogen to form hydrogen chloride, the empirical formula is corrected by adding 1 hydrogen atom to the formula to get the correct formula, $C_4H_4ClNO_2$.

Materials suitable for packing the chromatographic separation columns are well known, and any such packing material can be used that will perform the necessary separation with sufficient resolution to suit the integrating technique employed.

Any desired and convenient means may be employed for positioning the sample to be analyzed in the combustion tube or chamber 11. Likewise, although the substantially instantaneous ignition and very rapid combustion of the sample are absolutely critical to the successful practice of the method of this invention, any convenient and suitable means may be employed for igniting the sample. However, a combination means or device for positioning as well as supporting the sample in the combustion chamber 11, and for igniting that sample, has been developed and found to be particularly desirable. This combination means or device is illustrated in FIG. 3, wherein reference numerals which are the same as reference numerals in FIGS. 1 and 2 indicate like parts.

In FIG. 3, igniter 15 is shown as being constructed from a loop of Nichrome wire 105, the legs of which are sheathed in two adjacent and parallel lengths of very small-diameter Pyrex glass tubing 106 except for approximately the terminal 1 inch nearest the tip of the Nichrome wire loop shown as proximate the sample boat 14. This assembly, consisting of the loop of Nichrome wire 105 sheathed in two parallel, adjacent lengths of small-diameter Pyrex glass tubing 106, is mounted (at the end opposite the igniter tip) into a shorter length of larger-diameter Pyrex glass tubing 107, e.g., around 10 millimeters in diameter, which is drawn down to a lesser diameter at its inner end so that it can be installed into "tee" tube fitting 100 through Teflon ferrule 101a mating with threaded end 100a, as shown. This same assembly extends through "tee" fitting 100 sufficiently far so that the tip of the igniter 15, i.e., the end of the loop of wire 105 which serves as a supporting base for sample boat 14, is properly positioned in combustion tube or chamber 11 when the fitting 100 is attached to opening 5 in conduit 6 (as shown in FIGS. 1 and 2). To install the igniter 15, ferrule 101b which surrounds conduit 6 is engaged with the threads 100b on "tee" fitting 100, thus resulting in the proper positioning of igniter 15 and sample boat 14 in combustion tube or chamber 11 as shown in FIGS. 1 and 2. When installation is made, and the system has been sealed, i.e., by tightening each of ferrules 101a, 101b and 101c on threaded sections 100a, 100b and 100c, respectively, the apparatus is ready for use. The carrier gas, oxygen, is introduced as shown in FIG. 3 through conduit 3 and into "tee" fitting 100, and thence through conduit 6 into combustion tube or chamber 11.

In order to illustrate a specific and preferred embodiment of the method of the present invention, the method was carried out utilizing the apparatus illustrated in FIG. 1 to perform a multi-elemental microanalysis of a sample of the organic compound, p-bromobenzenesulfonyl chloride. A standard Model No. 154 Perkin-Elmer Vapor Fractometer was redesigned for use in this experiment. Details of the work involved in this redesign are given in a paper published by present applicants in *Chem. Instr.*, 6(1), 87 (1975). In brief, the standard detector cell was replaced with a new dual thermistor cell, and the carrier transport system was replaced with one allowing for dual column analysis. The heaters and heater circuits in the fractometer also were replaced to obtain higher oven temperature limits, and all standard fittings were replaced with stainless steel fittings. The flow of carrier gas was diverted to the exterior of the apparatus for connection to the microanalysis combustion system.

The primary combustion tube or chamber 11 employed in the experiment was constructed from 9 millimeter outside-diameter Vycor tubing, and was loosely packed with about a 1-inch section or plug of quartz wool 13 positioned approximately ¼ inch downstream of the tip of igniter 15. Igniter 15 was constructed as shown in FIG. 3 from Pyrex tubing and Nichrome wire. The Nichrome wire was of alloy type "A", had a diameter of about 0.040 inch, and was sheathed in two parallel and adjacent lengths of 2 millimeter outside-diameter Pyrex glass tubing 106, allowing the loop tip of the wire 105 to extend approximately 1 inch from the inner ends of the glass sheathing tubes 106. This whole assembly of wire 105 and sheaths 106 was in turn sealed into a shorter length of 10 millimeter diameter Pyrex glass tubing 107, which was drawn to an outside diameter of about 9 millimeters at its inside end so as to fit into threaded opening 100a of a ⅜ inch "tee" fitting 100. Externally-threaded end 100b of "tee" fitting 100 was connected to opening 5 in conduit 6 leading to combustion tube 11 by means of internally-threaded ferrule 101b. The tip of the igniter 15 extended into combustion tube 11 approximately 6 inches when so installed. The entire system was sealed by tightening threaded ferrules 101a and 101b against threaded end sections 100a and 100b, respectively.

The oxygen for combustion and to serve as the carrier gas was supplied through conduit 3 connected by threaded ferrule 101c to threaded end 100c of "tee" fitting 100, and thence through "tee" 100 and conduit 6 into combustion tube 11. The products of combustion were conducted through quartz wool plug 13, conduit 16, and into equilibrium tube 21, and thence through conduit 23, needle valve 25 which was set so as to maintain a back pressure in combustion tube 11 of approximately 10 p.s.i.g., and so as to control the rate of flow of oxygen at approximately 20 cubic centimeters per minute at about 27° C. and 10 p.s.i.g. Check valve 30 was provided in the flow train in order to prevent reverse flow when a partial vacuum is created at the peak of combustion in combustion tube 11.

Heat was supplied in combustion zone 10 to combustion tube 11 by means of a Dumas furnace which was adapted both for independent temperature control by means of a Variac controller, and for substantially instantaneous positioning around and removal from combustion tube 11. The heat in the equilibrium zone 20 was supplied by another Dumas furnace 22 which likewise was adapted both for substantially instantaneous positioning around and removal from equilibrium tube 21, and for independent heat control through a Variac controller. All connections, including valves, other fittings and conduits, beginning with conduit 23 and extending through the balance of the system were wrapped with a heating tape to prevent condensation of combustion products. The temperature of this tape also was controlled by a Variac controller, and was maintained at about 125° C.

The primary separating column 35 was a 3-foot length of 6 millimeter diameter tubing packed with 20 percent SE-30 on Chromosorb WAW 60/80 mesh adsorbent, 36, while the secondary separating column 45 was a 3-foot length of 6 millimeter diameter tubing packed with Chromosorb 102, 60/80 mesh, 46.

The contact combustion catalyst employed in the experiment was vanadium pentoxide powder, as manufactured and sold by Mathison, Coleman and Bell, of Norwood, Ohio, Catalog No. VX38, and having a specific surface area of 3.09 square meters per gram. Before use, this catalyst material was dried for approximately 8 hours at 120° C., and then stored over anhydrous calcium sulfate pending its use. The sample boat, identified by reference numeral 14 in FIG. 1, was a 3 millimeter aluminum boat obtained from Arthur H. Thomas and Company, Philadephia, Pa. Catalog No. 6495-C60. This boat also was dried for about 8 hours at 120° C., and then stored over anhydrous calcium sulfate pending its use. The organic compound from which the sample was drawn, i.e., the p-bromobenzene sulfonyl chloride, was reagent grade, and was dried at approximately 125° C. for 24 hours before use.

In accordance with the method of the present invention, a sample of p-bromobenzene sulfonyl chloride weighing exactly 1.463 milligrams was weighed and placed into the above-described aluminum sample boat. Approximately 50 milligrams of the vanadium pentoxide catalyst was added to the sample boat, and the ends of the boat were crimped closed prior to the boat's being placed on the loop or tip end of the igniter 15. The igniter 15 was then inserted into "tee" fitting 100, and the ferrule 101a was tightened on threaded section 100a to assure pressure-tight seal. Oxygen flow was initiated through conduit 3 in order to flush out the system including the combustion tube 11, the equilibrium tube 21, and the chromatograph separating columns and detector systems for about 2 minutes. The detector 40 was then turned on, and a stable base line was established.

By means of a tap key (not shown), the igniter 15 was connected to a central laboratory power supply set to deliver 15 volts D.C. at a maximum current of approximately 30 amps. The exposed tip of igniter 15 glowed cherry red in approximately 3 to 4 seconds after energization. Two seconds later, the oven 12 was positioned over the combustion tube 11, and the oven 22 was positioned over the equilibrium tube 21, as quickly as possible. Within a period of 10 seconds following energization of the igniter 15, the sample combusted with a flash. At the end of 20 seconds following its energization, the igniter 15 was disconnected and, after an additional 10 seconds, the oven 12 was removed from the combustion tube 11. The internal temperature of combustion tube 11 was maintained at about 700° C. while oven 12 was in position, while the internal temperature of the equilibrium tube 21 was maintained at about 625° C. while oven 22 was in position. The heating tape surrounding the various conduits, valves and other fittings was maintained at approximately 125° C.

Following deflagration of the sample, the chart in recorder 50, which chart was moving at a speed of 60 inches per hour, revealed peaks for water, sulfur dioxide, molecular iodine, carbon dioxide, hydrogen chloride and molecular bromine, as illustrated in FIG. 4. The several peaks on the chromatogram were physically cut out and weighed on a semimicro balance, and the following equations then were used to calculate the percentage elemental content:

Standardization:
$$\text{Response Factor (RF)} = \frac{\text{Weight of Peak (mg.)}}{\text{Sample Weight (mg.)} \times \text{\% Composition}}$$

Sample Composition:
$$\text{\% Sample Composition} = \frac{\text{Weight Peak (mg.)}}{\text{Sample Weight (mg.)} \times \text{Response Factor (RF)}}$$

Several changes in the detector attenuator setting were required, viz., 32x for bromine, to 16x for chlorine, back to 32x for carbon, to 16x for sulfur, and to 4x for hydrogen. After performing the steps and calculations indicated above, the following results were noted:

| Element | Weight % Found | Weight % Theory | Absolute Deviation, % |
|---|---|---|---|
| Carbon | 27.72 | 28.20 | 0.48 |
| Hydrogen | 1.05 | 1.19[a] | 0.14 |
| Chlorine | 13.21 | 13.87 | 0.66 |
| Bromine | 31.91 | 31.37 | 0.54 |
| Sulfur | 12.61 | 12.55 | 0.06 |

[a]Corrected for hydrogen chloride.

In order to illustrate another specific example of the practice of the method of the present invention, the apparatus employed with respect to the above-described specific example was expanded through the addition of a so-called nitrogen reduction train as illustrated in FIG. 2. Thus, the reduction tube or chamber 81 was constructed from a 10-inch length of 9 millimeter outside-diameter Vycor tubing, and was packed with about 3-inch segments of carbon powder (12 × 40 mesh) 82, and copper metal turnings 83, separated and held in place by quartz wool plugs 84. The inlet end of the reduction tube 81 was connected through conduit 67 to gas sampling valve 65, while the exit end of reduction tube 81 was connected through conduit 86 to a 3-foot Molecular Sieve 5A column using Teflon ferrules and a reducing union. This Molecular Sieve column was bent to fit into a 1 liter Dewar flask, and was connected through conduit 92 into secondary detector 60.

The gas sampling valve 65 was obtained from The Perkin-Elmer Corporation, of Norwalk, Conn., and had a Teflon seat in order to prevent air contamination of the sample during switching. As described hereinabove, the valve had two positions, viz., a normal position, during which an inert carrier gas, such as helium, flowed through and purged the system, and a sampling position, during which the gaseous combustion products in oxygen carrier gas were conveyed through the valve 65 and into the reduction tube 81.

In order to illustrate the operation of the method of this invention to determine the content of the element, nitrogen, in an organic material, a sample of exactly 1.476 milligrams of thioacetamide was accurately weighed and placed in an aluminum sample boat as described above in connection with the first experiment. The operation of the combustion train was in all respects substantially identical to that followed with respect to p-bromobenzene sulfonyl chloride. In particular, the flow rate of the oxygen carrier gas was maintained at about 20 cubic millimeters per minute measured at about 27° C. and 10 p.s.i.g., and with a back pressure of about 10 p.s.i.g. The temperature in the combustion tube 11 was maintained at about 700° C., while that in the equilibrium tube 21 was maintained at about 625° C. The primary separating column 35 (3 feet × 6 millimeters) was packed with a packing 36 consisting of Chromosorb 102 (60/80 mesh), while the secondary separating column 45 contained, as packing 46, plain glass beads. The oven 85 surrounding reduction tube 81 was set so as to maintain in said chamber a temperature of about 540° C. The flow rate of the inert carrier gas, helium, was set at 30 cubic centimeters per minute (measured at about 27° C. and about 20 p.s.i.g.), and to maintain a head pressure of from about 15 to about 20 p.s.i.g.

After combustion, and after the peak for carbon dioxide first appeared on primary recorder 50, the gas sampling valve 65 was switched so as to permit, for about 30 seconds, the flow of the combustion products in oxygen through conduit 67 and into reduction tube 81, and thereafter through conduit 86 and into Molecular Sieve 87, immersed in liquid nitrogen 91 contained in flask 90. The valve is then returned to "normal" position. The liquid nitrogen bath was removed in about 2 more minutes, and the Molecular Sieve was permitted to approach room temperature, causing the molecular nitrogen to be desorbed and to flow through conduit 92 and into and through secondary detector 60. Molecular nitrogen was reflected on secondary recorder 70 as a peak. When the area under this peak was measured and quantified, along with the areas under the peaks in recorder 50 corresponding to the products of the combustion of the other elements, the following results were obtained:

| Element | Weight % Found | Weight % Theory | Absolute Deviation, % |
|---|---|---|---|
| Carbon | 32.15 | 31.97 | 0.18 |
| Hydrogen | 7.09 | 6.71 | 0.40 |
| Nitrogen | 18.07 | 18.64 | 0.57 |
| Sulfur | 42.31 | 42.68 | 0.37 |

It should be appreciated that the method of the instant invention can be performed in apparatus and with materials and under conditions that vary somewhat from those described herein or illustrated in FIGS. 1, 2 and 3, and that limited variations in the method itself can be adopted without departing significantly from the concept of the invention. All such variations in apparatus, materials, conditions, or in the method, are contemplated as within the scope of the present invention.

The invention claimed is:

1. Method for the elemental analysis of an organic material to determine the content of each of the elements, carbon, hydrogen, sulfur, chlorine, bromine and iodine, said method comprising:

A. substantially instantaneously igniting and rapidly combusting a small sample of a known weight of said organic material in a combustion zone containing a contact catalyst and maintained at an internal temperature in the range of from about 675° C. to about 725° C., and through which zone a stream of oxygen continuously flows in greater than stoichiometric quantities and at a pressure in the range of from about 6 p.s.i.g. to not greater than about 10 p.s.i.g.;

B. conducting the gaseous mixture of oxygen and combustion products from said combustion zone through an equilibrium zone maintained at an elevated internal temperature sufficient to preclude substantially the formation of sulfur trioxide;

c. conducting the gaseous mixture of oxygen and combustion products from said equilibrium zone through gas chromatographic separation means whereby the combustion products of the said elements are separated each from the others; and D. conducting the effluent from said gas chromatographic separation means through a detector means which separately and quantitatively measures the amount of the combustion product of each of the said elements, from which amounts the content of each of said elements in said organic material may be calculated.

2. Method according to claim 1, wherein the internal temperature in said combustion zone is maintained at about 700° C.

3. Method according to claim 1, wherein the oxygen pressure in said combustion zone is maintained at about 10 p.s.i.g.

4. Method according to claim 1, wherein said contact catalyst is vanadium pentoxide.

5. Method according to claim 1, wherein said detector means is adapted to sense thermal conductivities.

6. Method according to claim 1, wherein the flow rate of oxygen into said combustion zone is in the range of from about 15 to about 35 cm³/min. at about 27° C. and at the pressure of said combustion zone.

7. Method according to claim 6, wherein said flow rate of oxygen is about 20 cm³/min. at about 27° C. and about 10 p.s.i.g.

8. Method according to claim 1, wherein the temperature in said equilibrium zone is maintained in the range of from about 580° C. to about 675° C.

9. Method according to claim 8, wherein said temperature is maintained at about 625° C.

10. Method for the elemental analysis of an organic material to determine its content of each of the elements, carbon, hydrogen, sulfur, chlorine, bromine, iodine and nitrogen, said method comprising:

A. substantially instantaneously igniting and rapidly combusting a small sample of a known weight of said organic material in a combustion zone containing a contact catalyst and maintained at an internal temperature in the range of from about 675° C. to about 725° C., and through which zone a stream of oxygen continuously flows in greater than stoichiometric quantities and at a pressure in the range of from about 6 p.s.i.g. to not greater than about 10 p.s.i.g.;

B. conducting the gaseous mixture of oxygen and combustion products from said combustion zone through an equilibrium combustion zone maintained at an elevated internal temperature sufficient to preclude substantially the formation of sulfur trioxide;

C. conducting the gaseous mixture of oxygen and combustion products from said equilibrium zone through gas chromatographic separation means whereby the combustion products of the said elements are separated each from the others;

D. conducting the effluent from said gas chromatographic separation means through a first detector means which separately and quantitatively measures the amount of the combustion product of each of the said elements, from which amounts the content of each of said elements in said organic material may be calculated;

E. conducting at least that portion of the effluent from said first detector means containing substantially all of the combustion products of nitrogen, first through a reduction zone containing an oxygen scavenger and a reducing agent and maintained at an internal temperature in the range of from about 500° C. to about 600° C., and then through a nitrogen-adsorption zone maintained at a temperature of not greater than about −30° C.;

F. conducting a stream of an inert gas through said nitrogen-adsorption zone while raising the temperature of said nitrogen-adsorption zone to about normal room temperature; and G. conducting the effluent from said nitrogen-adsorption zone through a second detector means which quantitatively measures the amount of nitrogen in said sample, from which amount the nitrogen content of said organic material may be calculated.

11. Method according to claim 10, wherein said oxygen scavenger is carbon.

12. Method according to claim 10, wherein said reducing agent is copper.

13. Method according to claim 10, wherein the temperature in said reduction zone is maintained at about 540° C.

14. Method according to claim 10, wherein said inert gas is helium.

15. Method according to claim 10, wherein said first and second detector means are adapted to sense thermal conductivities.

* * * * *